United States Patent [19]

Duplantis

[11] Patent Number: 4,921,344
[45] Date of Patent: May 1, 1990

[54] APPARATUS AND METHOD FOR ENHANCING THE IMAGES OF INTRA-ORAL PHOTOGRAPHY

[76] Inventor: Shannon S. Duplantis, 3701 James Dr., Metairie, La. 70003

[21] Appl. No.: 743,824

[22] Filed: Jun. 12, 1985

[51] Int. Cl.$^5$ .................... G03B 15/03; G03B 29/00; F21V 17/02
[52] U.S. Cl. .................... 354/62; 354/149.1; 354/149.11; 362/16; 362/323
[58] Field of Search ............ 354/62, 149.1, 141, 354/126, 149.11; 362/16, 18, 319, 322, 323

[56] References Cited

U.S. PATENT DOCUMENTS

| | | | |
|---|---|---|---|
| 3,382,781 | 5/1968 | Hamilton | 354/62 |
| 3,388,645 | 6/1968 | Sullivan | 354/62 |
| 3,424,070 | 1/1969 | Nyman | 354/62 |
| 3,479,937 | 11/1969 | Sullivan | 354/62 X |
| 3,884,222 | 5/1975 | Moore | 354/62 X |
| 4,085,436 | 4/1978 | Weiss | 362/16 |
| 4,425,599 | 1/1984 | Rieder et al. | 362/322 X |
| 4,519,018 | 5/1985 | Rowland | 362/323 X |

*Primary Examiner*—Michael L. Gellner
*Attorney, Agent, or Firm*—John W. Carpenter

[57] ABSTRACT

An apparatus for a camera utilized in intra-oral photography including a lens housing which mounts to the camera. A lens is positioned within the lens housing, and a circular flash with a transparent face and having an inner circumference and an outer circumference generally circumscibes the lens and is secured to the lens housing. A shield is removably positioned over a portion of the circular flash for blocking out a predetermined portion of the illumination from the circular flash from a circular illuminated flash into a directional or point illuminated flash. The shield includes a flange section and a lens shield section integrally bound to the flange section. A process for improving the quality of the image photography with a camera having a flash including the step of shielding a predetermined portion of the flash in order to block out a portion of the illumination in order to convert the flash from a circular flash into a directional or point flash, and photographing the intra-oral image to be photographed from a non-metallic mirror that has been positioned in a predetermined location in a person's mouth.

25 Claims, 4 Drawing Sheets

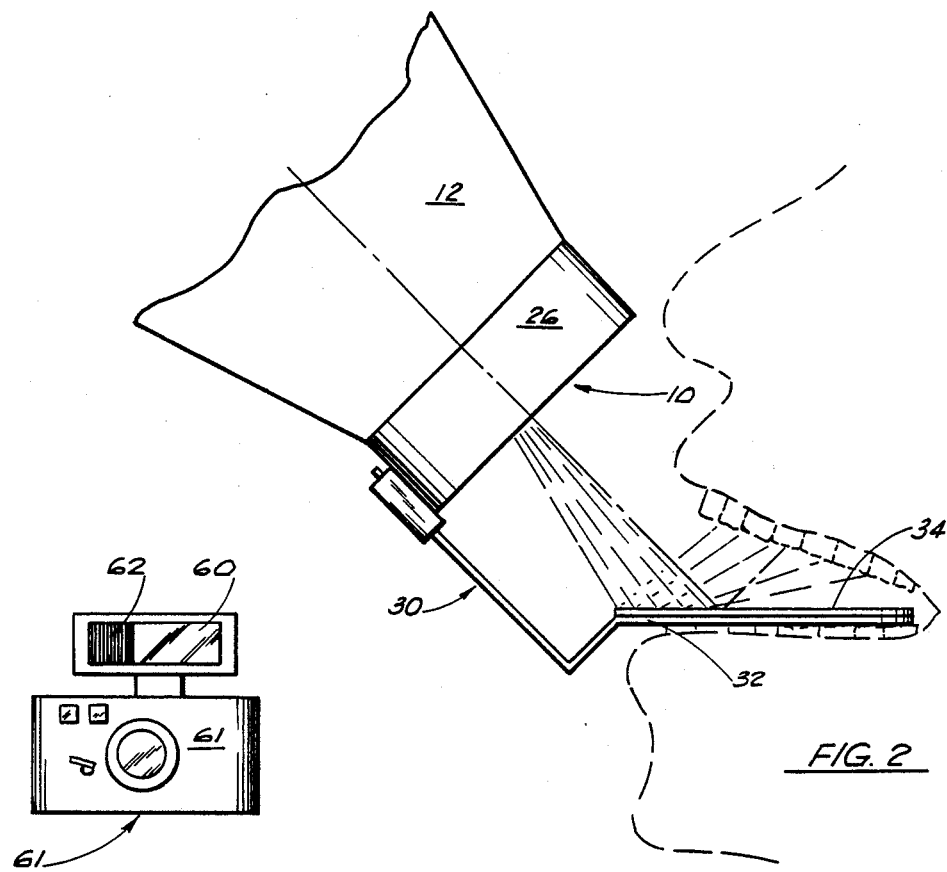
FIG. 2
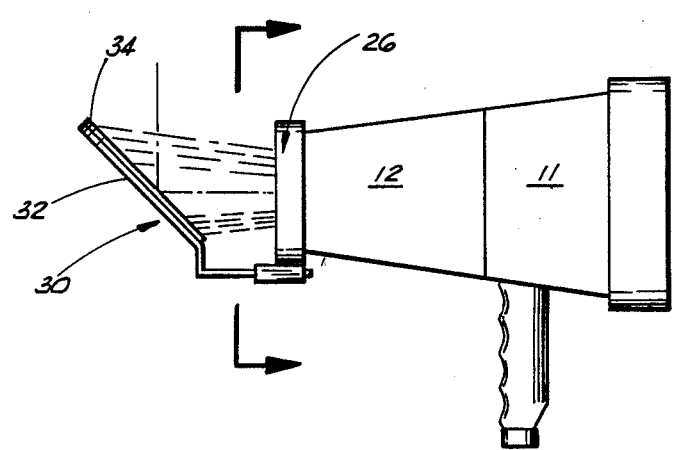
FIG. 1
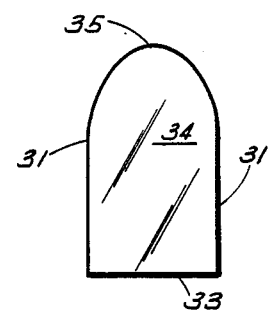
FIG. 4
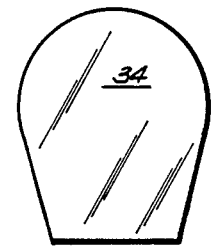
FIG. 5
FIG. 3

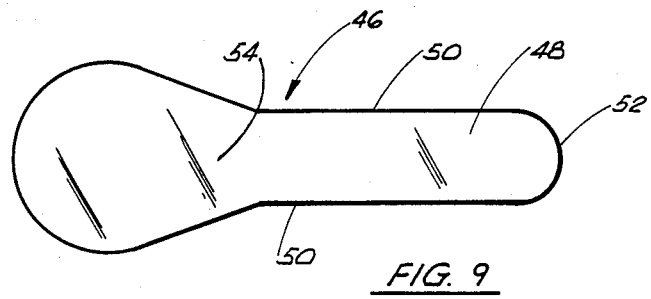
FIG. 9
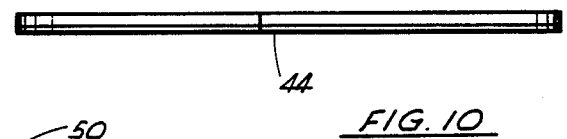
FIG. 10
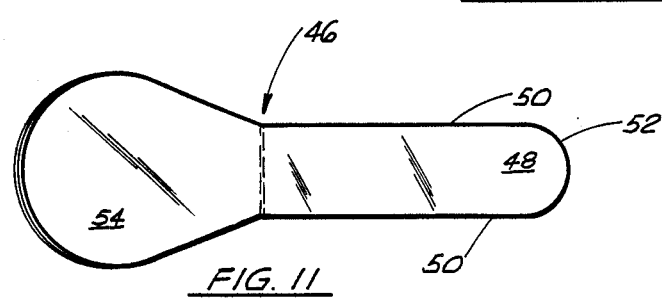
FIG. 11
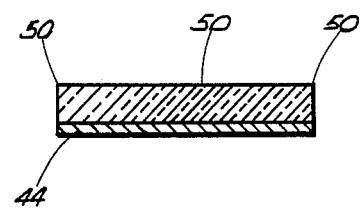
FIG. 13
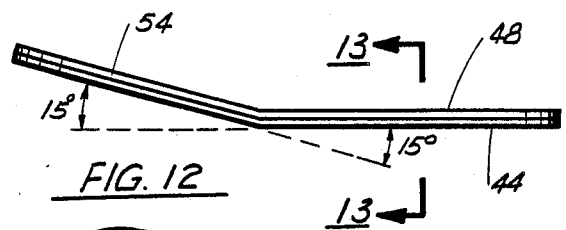
FIG. 12
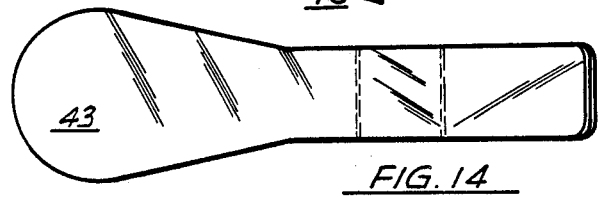
FIG. 14
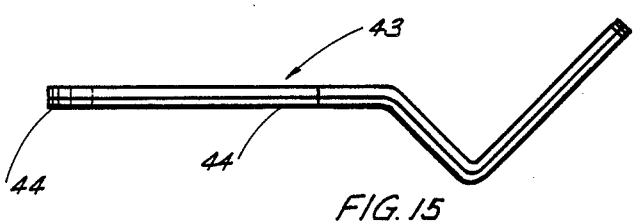
FIG. 15
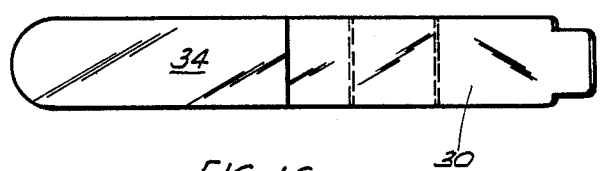
FIG. 16
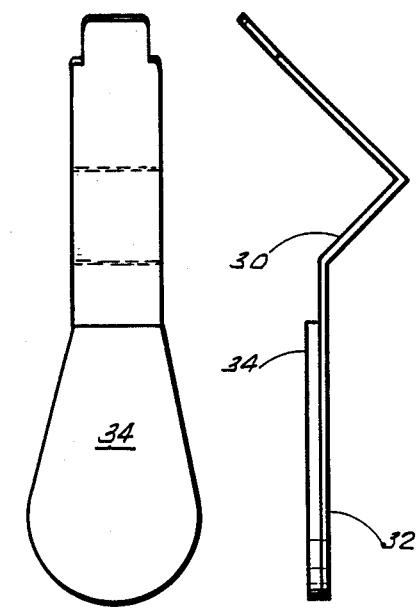
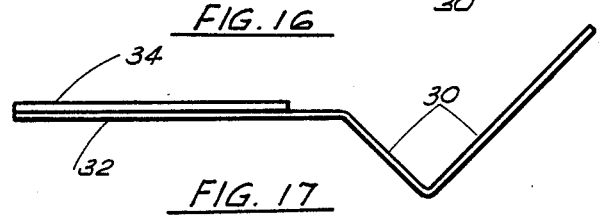
FIG. 17
FIG. 18  FIG. 19

APPARATUS AND METHOD FOR ENHANCING THE IMAGES OF INTRA-ORAL PHOTOGRAPHY

BACKGROUND OF THE INVENTION

1. Field of the Invention

This invention relates to improving the quality of the image photographed with a camera having a flash. More specifically, this invention provides an apparatus and process for enhancing the image photographed in intra-oral photography.

2. Background of the Invention

In the art of oral photography, metallic mirrors and circular flashes are generally utilized. Metallic mirrors cause distortions in intra-oral photographs. Circular illuminations emanating from a circular flash is essentially dispersed and affects the quality of intra-oral photography.

Therefore, what is needed and what has been invented by me is an apparatus and method for enhancing the images of intra-oral photography which do not include the foregoing deficiencies.

SUMMARY OF THE INVENTION

It is an object of this invention to provide an apparatus and process for improving the quality of the image photographed with a camera having a flash.

It is another object of the invention to provide an apparatus and process for enhancing the image photographed in intra-oral photography.

It is still yet another object of this invention to provide a novel mirror which is used in intra-oral photography.

Still further objects of the invention will be recognized by those possessing ordinary skill in the art.

This invention accomplishes its desired object by providing an apparatus for a camera utilized in intra-oral photography comprising a lens housing means which mounts to the camera. A lens means is positioned within the lens housing, and a circular flash means with a transparent face and having an inner circumference and an outer circumference generally circumscribes the lens means and is secured to the lens housing means. A shield means is movably positioned over a portion of the circular flash means for blocking out a predetermined portion of the illumination from the circular flash in order to convert the flash emanating from the circular flash means from a circular illuminated flash into a directional or point flash. The shield means comprises a flange section means and a lens shield section means integrally bound to the flange section means. This invention further accomplishes its desired objects by providing a process for improving the quality of the image photographed with the camera means having a circular flash means comprising the step of shielding a predetermined portion of the illumination in order to convert the flash from the circular flash into a directional or point flash, and photographing the intra-oral image to be photographed from a non-metallic mirror means that has been positioned in a predetermined location in a person's mouth.

BRIEF DESCRIPTION OF THE DRAWINGS

FIG. 1 is a front elevational view of a camera having a shield blocking partially a flash;

FIG. 2 is a partial side elevational view of a camera having its lens directed towards the mirror surface of a non-metallic mirror positioned in a person's mouth;

FIG. 3 is a complete side elevational of a camera having its lens directed towards the mirror face of a non-metallic mirror;

FIG. 4 is a top plan view of a buccal view mirror attachment for the mirror mount;

FIG. 5 is a top plan view of an occlusal view mirror attachment for the mirror mount;

FIG. 9 is a top plan view of a hand held mirror;

FIG. 10 is a side elevational view of the hand held mirror of FIG. 9;

FIG. 11 is a top plan view of another hand held mirror;

FIG. 12 is a side elevational view of the hand held mirror of FIG. 11;

FIG. 13 is a vertical sectional view taken in direction of the arrows and along the plane of line 13—13 in FIG. 12;

FIG. 14 is a top plan view of an embodiment of the mirror of this invention;

FIG. 15 is a side elevational view of the mirror of FIG. 14;

FIG. 16 is a top plan view of one embodiment of the mirror mount and the non-metallic mirror;

FIG. 17 is a side elevational view of the embodiment of the mirror mount of FIG. 16;

FIG. 18 is a top plan view of another embodiment of the mirror mount and the non-metallic mirror; and FIG. 19 is a side elevational view of the embodiment of the mirror mount of FIG. 18.

DETAILED DESCRIPTION OF THE INVENTION

Figure 6:
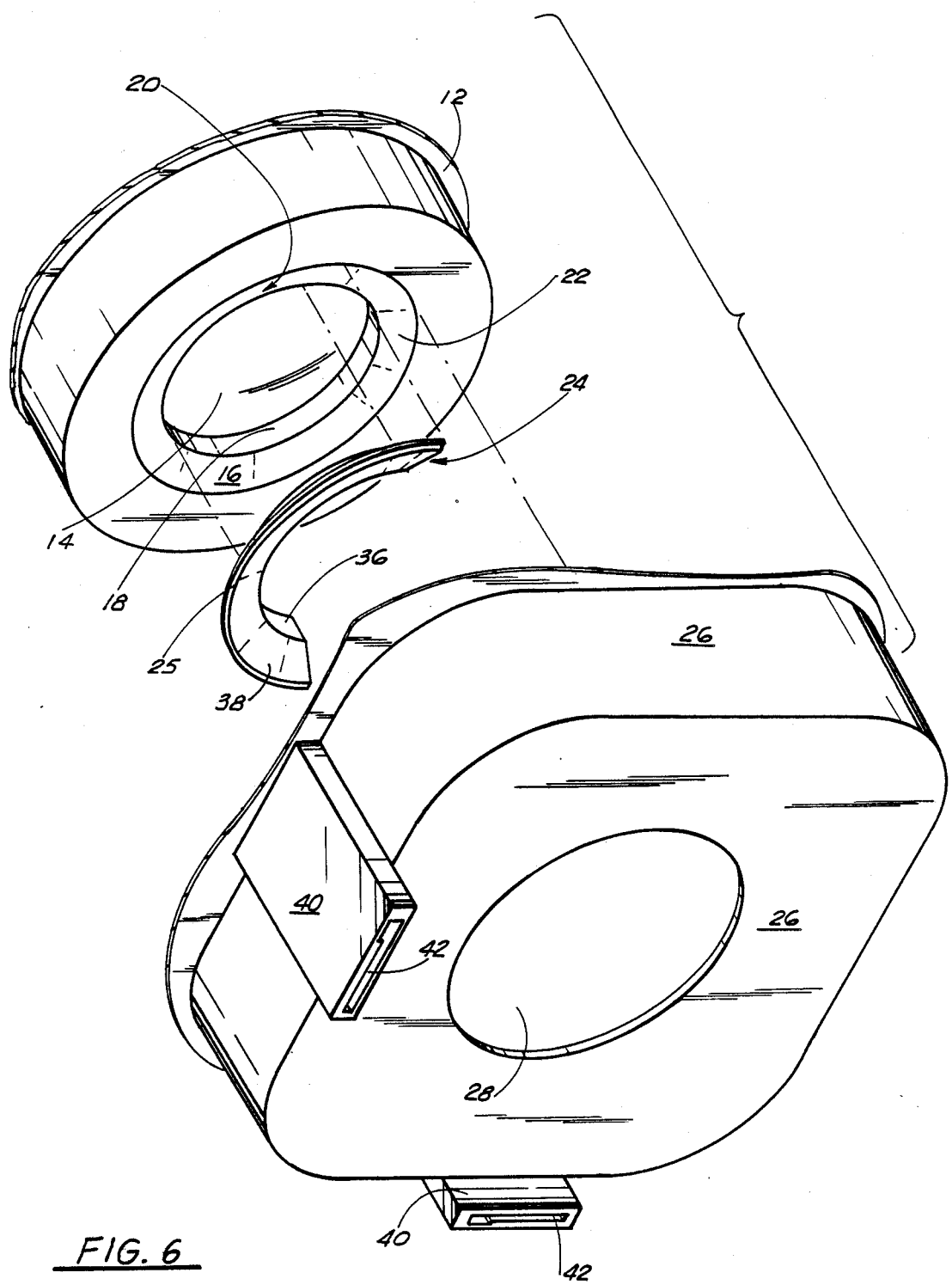
FIG. 6 is an exploded segmented perspective view of the lens housing, the shield and the intra-oral mount.

Referring in detail now to the drawings wherein similar parts of the invention are identified by like reference numerals, there is seen an apparatus, generally illustrated as 10, for a camera body 11 and utilized in intra-oral photography. Apparatus 10 includes a lens housing 12 which is mounted on the camera body 11, and a lens 14 positioned within the lens housing 12. A circular flash, generally illustrated as 16, generally circumscribes the lens 14, and is secured to the lens housing 12. Circular flash 16 is electrically connected to a power source (e.g., a battery) and is activated or illuminated in accordance with procedures well known as those possessing ordinary skill in the art. Circular flash 16 has an inner circumference 18, an outer circumference 20, and a transparent face 22. A shield, generally illustrated as 24, is movably positioned over a portion of the circular flash 16 for blocking out a predetermined portion of the illumination from the circular flash 16 in order to convert the flash 16 into a directional or point flash. The shield 24 (see FIG. 6) has a flange outer circumference 25 and includes a flange section 36 which flushes against the inner circumference 18 of the circular flash 16, and a lens shield section 38 integrally bound to the flange section 36. The lens shield section 38 movably traverses the transparent face of the circular flash 16 and generally defines an arc of between about 90° and about 270° (see FIGS. 6, 7, and 8). In a preferred embodiment of the invention, the lens shield section 38 defines an arc of about 180° (see FIG. 8).

The apparatus 10 additionally includes an intra-oral mount, generally illustrated 26, that is mounted on the lens housing 12 (see FIGS. 2 and 3). Intra-oral mount 26 has an opening 28 (see FIG. 6) that generally registers circumferentially with the outside circumference 20 of the circular flash 16 and assist in movably securing the shield 24 over the circular flash 16 when the perimeter of the opening 28 presses against the flanged outer circumference 25 of the shield 24.

Figure 7:
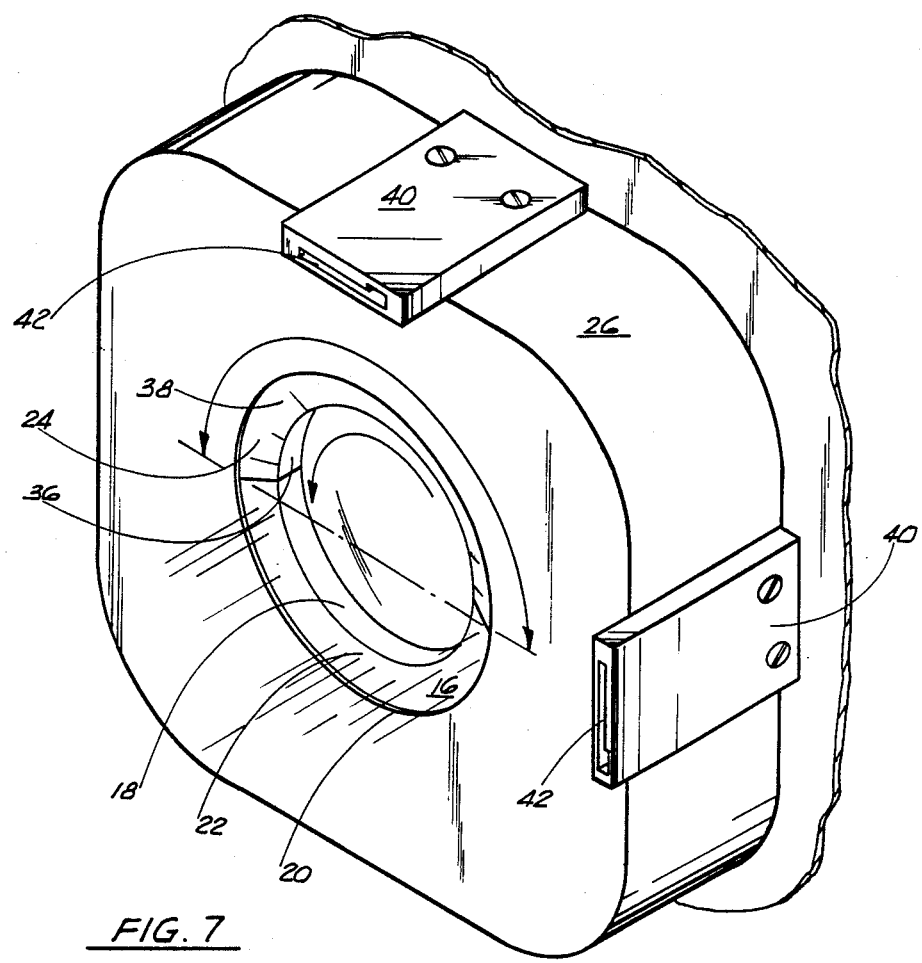
FIG. 7 is an enlarged perspective view of the intra-oral mount positioned around the lens housing with the shield rotatably positioned in place around the circular flash.
Figure 8:
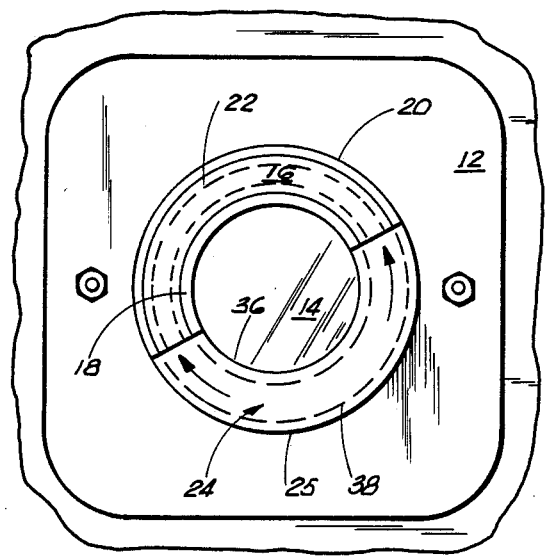
FIG. 8 is a front elevational view of the lens housing with the shield rotatably positioned along the face of the circular flash.

A mirror mount, generally illustrated as 30, is removably attached to the intra-oral mount 26, preferably through the use of a mount holder 40 which has a structure defining a slot 42. An end of the mirror mount 30 removably slidably lodges in the slot 42 in order to be mounted on the lens housing 12. In a preferred embodiment of the invention, these are two mirror mount holders 40—40 secured to the intra-oral mount 26 along adjacent edges thereof as represented in FIG. 6 and FIG. 7. Positioning of the mirror mount holders 40—40 as such facilitates the picturing of part of a person's mouth. The mirror from the intra-oral mount 26 is represented in FIG. 2 and 3 such that an end section 32 is 2 is available for insertion into an oral cavity (represented as dotted lines in FIG. 8).

Prior art mirror mounts 30 are constructed of metals and has the end section 32 polished or coated to define a mirror. I have discovered that a metallic mirror end section 32 causes distortion in the intra-oral photographs taken with the use of my invention, because a metal mirror has metal dead surface that lowers the quality of the image photographed. To correct these distortions, I have discovered that by mounting a non-metallic mirror 34 to the end section 32 of the mirror mount 30, the images photographed are sharpened or enhanced. Non-metallic mirror 34 may be manufactured of any material whose surface can receive a material that is used for coating the reflective surface which forms an image of an object when light rays coming from that object fall upon it. In a preferred embodiment of the invention, mirror 34 is a plate glass having a surface coated with tin mixed with mercury, or more preferably, with silver or aluminum which are vacuum-deposited or sputtered into the surface. Mirror 34 may also be silver coated by reducing AgNO₃ solutions with reducing solutions on its glass surface, that is pretreated with stannous choloride. The reducing solutions include sugar, rochelle salts, or formaldehyde, well known to those in the art.

The mirror 34 of this invention is intended for critical use and requires the use of front or top-surface reflectors, with the reflecting coating being on the exposed front or top surface of the glass. Most mirrors are intended for noncritical uses, such as looking glasses or wall mirrors, and will have the reflecting metallic coating placed on the back side of the glass, this using the glass to protect the coating from oxidations by the atmosphere. In another preferred embodiment of the invention, I have discovered that mirror 34 may be manufactured of plastic origin such as polyethylene, polypropylene, styrene, ABS, or any other plastic polymers means that can receive and retain a front or top-surface reflective coating. The most preferred plastic origin material for mirror 34 is that sold under the trademarks "Plexiglass" by Rohn & Hass Co. and is thermoplastic poly-(methyl methacrylate)-type polymer that is readily available in sheet form.

Mirror 34 has two forms or shapes of embodiment. For a buccal view of an oral cavity, mirror 34 will be defined by the buccal view attachment of FIG. 4 which has a pair of parallel sides 31—31, a side 33 normal to the parallel sides 31—31, and a generally semi-circular side 35 opposed to side 33. For an occlusal view of an oral cavity, mirror 34 will be the occlusal view attachment of FIG. 5 which is essentially truncated tear-drop in shape. Mirror 34 may have its back or bottom surface bounded to the mirror mount 30 by any known or suitable means such as by glue or the like. FIGS. 16 and 17 illustrate the buccal view attachment embodiment of mirror 34 mounted on the mirror mount 30. FIGS. 18 and 19 depict the occlusal view embodiment of the mirror 34 secured on the mirror mount 30.

It should be understood that non-metallic mirror 34 would not be necessary for mounting on metallic mirror mount 30 if the mirror mount 30 itself was manufactured of one of the previously mentioned non-metallic materials which embodies mirror 34. Thus, mount 30 would be non-metallic and would be removably secured to the intra-oral mount and protrude therefrom such that an end section thereof is eventually injected into an oral cavity. For purposes of illustration, a non-metallic mount 30 has been generally illustrated as 43 in FIGS. 14 and 15 and is defined as a mirror 43. The non-metallic end section of mirror 43 that is to be injected into an oral cavity has a surface that defines a mirror surface. This mirror surface may be the result of coating the non-metallic end section with silver or aluminum in accordance with the previously mentioned procedure that is well known. In this embodiment of the invention, if a mirror mount holder 40 is secured to the intra-oral mount 26, the non-metallic mirror 43 would be slidably removably lodged into the slot 42. FIGS. 14 and 15 are also representative illustration of the non-metallic mirror 43 wherein the end section that goes into an oral cavity is of the occlusal type. It is important to note that in the event that this embodiment of the invention is being utilized, I have discovered that the back or bottom surface of the end section having a mirror surface of the mirror 43 has to have an opaque covering 44 under and/or over the entire back or bottom surface of the mirror surface. FIG. 15 illustrates and depicts the opaque covering 44 as being over the entire structure of the mirror 43; this is not necessary. All that is necessary is that the back or bottom surface opposed to the mirror surface that goes into the oral cavity has the opaque covering 44. If the opaque covering 44 is omitted, the image photographed will not have the same quality as those images photographed with the opaque covering 44 included. Perhaps one of the apparent reasons for this is that the non-metallic mirror 43 is constructed in a preferred embodiment of a material including glass, plexiglass, or the like, that has structure which allows the passage of light, especially through the material structure underneath the mirror surface, the passage of light through the material structure, and against the underneath side of the reflective mirror coating apparently affects perhaps the quality of the images being photographed with my invention that is used in intra-oral photography.

Opaque covering 44 may be any type or suitable covering that readily adheres to the back or bottom surface opposed to the surface that has the reflective mirror coating. In a preferred embodiment of the invention, opaque covering 44 is a vinyl, preferably fireproof, opaque strip that has been adhered to the back of the mirror 43 or even black paint means which has been placed thereon.

In another embodiment of my invention, instead of using the metallic mirror mount 30 including the non-metallic mirror 34 mounted therein as was previously described or the mirror 43 of FIGS. 14 and 15 with the opaque covering 44, the hand held mirrors of FIG. 9–13, generally illustrated as 46, may be utilized in combination with the remaining features of my invention. Mirror 46 includes a buccal portion 48 having a pair of essentially parallel edges 50—50 that mates with a generally semi-circular edge 52. An occlusal portion 54 is integrally bound to the buccal portion 48, and is defined as generally a truncated tear-drop with the truncation edge being bound to the buccal portion 48 along an edge of a buccal section opposed to the semi-circular edge. The buccal 48 and the occlusal portion 54 are available to be inserted into an oral cavity for intra-oral photography.

As was the case for the non-metallic mirror 34 bound to the end section 32 of the mirror mount 30 and the case for the non-metallic mirror 43, mirror 46 can not be manufactured of metal and preferably comprises a non-metallic material selected from the group consisting of glass, plexiglass, a plastic polymer, or any other non-metallic material that can receive and retain a reflective mirror coating. Preferably mirror 46 comprises glass or plexiglass; more preferably, mirror 46 comprises plexiglass. The buccal 48 and the occlusal portion 54 each has a front or top-surface that defines a mirror surface originating from a reflective coating, and evidenced in FIGS. 9 and 11. As was the case for the non-metallic mirror 43 and perhaps apparently for the same reason that has been assigned thereto, the back or bottom surface of mirror 43 that is opposed to the mirror surface of same, has to have the opaque covering 44 under and/or over the entire back or bottom surface of the buccal 48 and the occlusal portion 54.

The surface with the opaque covering 44 of the buccal portion has a buccal plane, and the surface with the opaqued covering 44 of the occlusal portion has an occlusal plane which in a preferred embodiment of the invention, is angularly disposed from between about 0° and 45° with the buccal plane. More preferably, the occlusal plane of the occlusal portion defines an about 15° angle with the buccal plane of the buccal portion FIG. 10 and FIG. 12, respectively, represent the 0° and the preferred 15° angular disposement of the occlusal plane with the buccal plane. I have discovered that there is criticality in the amount of degrees between the occlusal plane and the buccal plane with respect to the quality of photographs taken with mirror 46. If there is a greater than a 45° angle between the occlusal plane and the buccal plane, or stated another way, if there is too much bend between the occlusal portion and the buccal portion, I have discovered that the photographs taken with the mirror 46 have "hot spots". The more or greater the angle disposement between the occlusal and the buccal plane, or the more bend between the occlusal portion and the buccal portion, the more apt that "hot spots" will develop on photographs taken with the mirror 46.

With continuing reference to the drawings for operation of the invention and the method for improving the quality of an intra-oral image photographed, non-metallic mirror 34 is bound to the surface of the end section 32 of the mirror mount 30, which also has an end slidably lodged in slot 42 of one of the mount holders 40. The shield 24 is revolved around the circular flash 16 until a predetermined position is reached in order to block out a predetermined portion of the illuminations in order to convert the illuminations emanating from the flash 16 into a directional or point flash. It should be understood that while a preferred embodiment is to block out or shield the circular flash 16 of the invention, the theory of my invention with respect to intra-oral photography is just as applicable to a flash 60 mounted on a camera 61 (e.g., 35 mm) and having a shield 62 (see FIG. 1) which shields a predetermined portion of the flash emanating from the flash 60. My invention is operable with the camera 61 and utilization of one of the hand held mirrors 46.

The end section 32 including one of the mounted non-metallic mirrors 34 of FIGS. 4 or 5 is positioned in a predetermined location within the oral cavity of a person's mouth (e.g., see FIG. 2). The lens 14 of the camera 11, which is preferably a polariod type, is directed to the mirror face or surface of the mirror 34, as illustrated in FIGS. 2 and 3. After the end section 32 is postured in the predetermined location and the desired teeth to be photographed are reflected from the mirror surface of non-metallic mirror 34, the shutter (not shown in the drawing) is depressed which subsequently activates the circular flash 16 from a hidden power source (i.e., a battery) and the teeth image(s) being reflected off the mirror surface of non-metallic mirror 34 and through the lens 14 are photographed with the camera 11. The procedure would be the same if the mirror mount 30, including the attached mirror 34, was replaced with the mirror 43 of FIGS. 14 and 15.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth.

I claim:

1. An apparatus for a camera utilized in intra-oral photography comprising a lens housing which mounts to camera; a lens positioned within said lens housing; a circular flash with a transparent face and having an inner circumference and an outer circumference in generally circumscribing said lens means and secured to said lens housing; and a shield means without a rotatable shaft mounted thereto and having a lens shield section movably positioned over a portion of the circular flash for blocking out a predetermined portion of illumination from the circular flash in order to uniformly convert the flash emanating from the circular flash from a circular illuminated flash into a directional or point illuminated flash without obstructing a photographic image that passes through the lens.

2. The apparatus of claim 1 additionally including an intra-oral mount with an opening and mounted on the lens housing such that the opening generally registers with the outside circumference of the circular flash and assist in movably securing the shield over the circular flash.

3. The apparatus of claim 2 additionally comprising at least one mirror mount removably attached to said intra-oral mount and protruding therefrom such that an end section thereof is eventually generally inserted into an oral cavity; and a non-metal mirror bound to said end section of said mirror mount in order to enhance or sharpen the image photographed.

4. The apparatus of claim 3 additionally comprising at least one mirror mount holder secured to said intra-oral mount, said mirror mount holder having a structure defining a slot; and said mirror mount slidably removably lodges in said slot of said mirror mount holder in order to be mounted on said intra-oral mount.

5. The apparatus of claim 4 wherein two mirror mount holders are secured to said intra-oral mount along adjacent edges thereof.

6. The apparatus of claim 5 wherein said mirror comprises glass having a surface that defines a mirror surface.

7. The apparatus of claim 5 wherein said mirror comprises plexiglass having a surface that defines a mirror surface.

8. The apparatus of claim 2 wherein said shield comprises a flange section which flushes against the inner circumference of the circular flash; and a lens shield section integrally bound to the flange section.

9. The apparatus of claim 8 wherein said lens shield section movably traverses the transparent face of said circular flash and generally defines an arc of between about 90° and about 270°.

10. The apparatus of claim 2 additionally comprising a mirror means removably secured to the intra-oral mount and protuding therefrom such that an end section thereof is eventually generally inserted into an oral cavity, said mirror means comprises a non-metallic material selected from the group consisting of glass, plexiglass, plastic means, or any non-metallic material that can receive and retain a reflective mirror coating; and said end section that is inserted into an oral cavity having a surface that defines a mirror surface and an opaque covering means covering the back or bottom surface of said end section opposed to the surface that defines the mirror surface.

11. The apparatus of claim 10 wherein said shield means comprises a flange section means which flushes against the inner circumference of the circular flash means; and a lens shield section means integrally bound to the flange section means.

12. The apparatus of claim 11 wherein said lens shield section means movably traverses the transparent face of the circular flash means and generally defines an arc of between about 90° and about 270°.

13. The apparatus of claim 12 additionally comprising at least one mirror mount holders secured to said intra-oral mount holder having a structure defining a slot; and said mirror means slidably removably lodges in said slot of said mirror mount holder.

14. The apparatus of claim 13 wherein two mirror mount holders are secured to the intra-oral mount means along adjacent edges thereof.

15. The apparatus of claim 1 wherein said shield means comprises a pair of essentially parallel, arcuate edges, and said lens shield section means is formed with no openings or slots.

16. An apparatus for a camera utilized in intra-oral photography comprising a lens housing means which mounts to said camera; a lens means positioned within said lens housing; a circular flash means with a transparent face and having an inner circumference and an outer circumference in generally circumscribing said lens means and secured to said lens housing means; a shield means movably positioned over a portion of the circular flash means for blocking out a predetermined portion of the illumination from the circular flash in order to convert the flash emanating from the circular flash from a circular illuminated flash into a directional or point illuminated flash; and an intra-oral mount means with an opening mounted on the lens housing means such that the opening generally registers with the outside circumference of the circular flash means and assist in movably securing the shield means over the circular flash means.

17. The apparatus of claim 16 wherein said shield means comprises a flange section means which generally flushes against the inner circumference of the circular flash means.

18. The apparatus of claim 16 additionally comprising at least one mirror mount means removably attached to said intra-oral mount and protruding therefrom such that an end section thereof is eventually generally inserted into an oral cavity; and a non-metal mirror means bound to said end section of said mirror mount means in order to enhance or sharpen the image photographed.

19. An apparatus for a camera utilized in intra-oral photography comprising a lens housing means which mounts to said camera; a lens means positioned within said lens housing; a circular flash means with a transparent face and having an inner circumference and an outer circumference in generally circumscribing said lens means and secured to said lens housing means; and a shield means comprising a flange section means which generally flushes against the inner circumference of the circular flash means and a lens shield section means integrally bound to the flange section means and movably positioned over a portion of the circular flash means for blocking out a predetermined portion of the illumination from the circular flash in order to convert the flash emanating from the circular flash means from a circular illuminated flash into a directional or point illuminated flash.

20. The apparatus of claim 19 additionally including an intraoral mount means with an opening and mounted on the lens housing means such that the opening generally registers with the outside circumference of the circular flash means and assist in movably securing the shield over the circular flash means.

21. The apparatus of claim 20 additionally comprising at least one mirror mount means removably attached to said intra-oral mount and protruding therefrom such that an end section thereof is eventually generally inserted into an oral cavity; and a non-metal mirror means bound to said end section of said mirror mount means in order to enhance or sharpen the image photographed.

22. A process for improving the quality of an intra-oral image photographed with a camera means having a circular flash means with an inner circumference and an outer circumference comprising the steps of:

(a) forming a shield means having an outer arcuate edge with a predetermined length and an inner arcuate edge having a shorter length than the length of the outer arcuate edge, and such that the outer arcuate edge are capable of respectively generally registering with the outer circumference and the inner circumference of the circular flash means when the shield means is positioned over the circular flash means;

(b) positioning the shield means over the circular flash means such that the outer arcuate edge and the inner arcuate edge generally register with the outer circumference and the inner circumference respectively of the circular flash means and a predetermined portion of any illumination emanating from the circular flash means is blocked out to convert the illumination into a directional or point flash;

(c) illuminating the circular flash means, which has been partially blocked by the shield means, to reflect a directional or a point flash off a non-metallic mirror means that has been positioned in a predetermined location in a person's mouth such that the camera means receives and photographs a sharper intra-oral image off the non-metallic mirror means was utilized or a shield means not utilized.

23. The process of claim 22 additionally comprising forming the shield means with a flange section means which is generally flushed against the inner circumference of the circular flash means when said shield means is positioned over the circular flash means.

24. The process of claim 23 additionally comprising the back of said non-metallic mirror means with an opaque means.

25. The process of claim 24 wherein said mirror means comprises a non-metallic material selected from the group consisting of glass, plexiglass, plastic means, or any non-metallic material that can receive and retain a reflective mirror coating.

* * * * *